W. H. CUTLER.

Inhalers.

No. 5,449. Reissued June 17, 1873.

Witnesses

B. H. Smith
S. Noyes.

Inventor

William H. Cutler

AM. PHOTO-LITHOGRAPHIC CO. N.Y. (OSBORNE'S PROCESS.)

UNITED STATES PATENT OFFICE.

WILLIAM H. CUTLER, OF BUFFALO, NEW YORK.

IMPROVEMENT IN INHALERS.

Specification forming part of Letters Patent No. 135,411, dated February 4, 1873; reissue No. 5,449, dated June 17, 1873; application filed May 13, 1873.

*To all whom it may concern:*

Be it known that I, WILLIAM H. CUTLER, of the city of Buffalo, in the county of Erie, and State of New York, have invented a certain new and useful Portable Inhaling-Tube, and I do hereby declare that the following is a full and exact description thereof:

The principal defects of the tubular inhalers heretofore employed are the permanent alteration of the structure of the porous filling or absorbent material under the action of the more concentrated forms of liquid medicines, and the constant change of form—*i. e.* shrinking and swelling—that goes on in such material when the inhaler is being used, according to the amount of liquid held absorbed by it.

By a long series of experiments, I have demonstrated that filtering or unsized paper remains practically unaltered by powerful medicines; and also that in the form of tubes, such paper or analogous material, will insure an almost unvarying area of air and liquid contact-surface, so that the quantity of medicine inhaled in a given time (and approximately its effect) may be determined beforehand with great accuracy.

In carrying out my invention, I form the core or filling of the inhaling instrument of one or more tubes, made of the aforesaid fibrous and capillary or porous material, so arranged that the air contained in and circulating through them will be charged with the medical compound previously absorbed.

Figure 1:
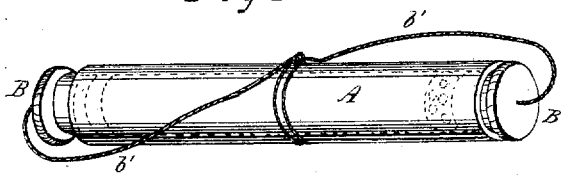
Figure 2:
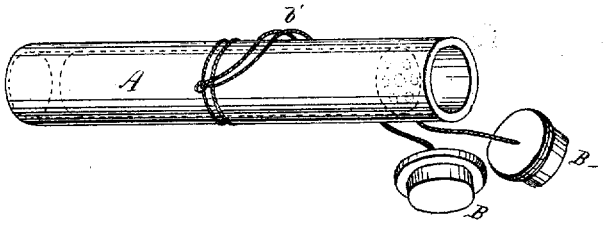
Figure 3:
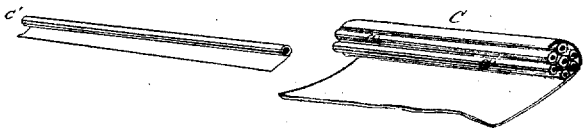

In the accompanying drawing, Figure 1 represents a perspective view of the instrument when stoppered. Fig. 2 represents the same when open for inhalation. Fig. 3 represents the core, showing the details of construction.

A represents an ordinary inhaling tube or casing, which may be made as usual of glass, silver, or such other material as will effectually resist the action of an acid or other medical compound which may be brought into contact therewith. This tube or casing is open at both ends as shown, each opening being provided with a stopper, B, which is suspended and connected by a cord, *b'*, to the body of the instrument. C represents the subject of my invention, viz., the core or filling of the tube or casing, which core is made of filtering-paper or other analogous capillary or porous substance, and consists of one or more tubes, C' preferably held together or surrounded by an outer wrapping of the same material.

In order to charge my inhaler, a few drops—say twenty-five to fifty—of the solution or medical compound are introduced through one or both ends of the tube, opened for that purpose. The fluid so introduced will immediately enter the material of which the core is made, and be held there ready for use.

The principal advantages of my invention over others lie, first, in its retaining its form, absorbent power, and flexibility, neither shrinking or swelling, nor becoming perceptibly denser, nor otherwise essentially altered in structural character under the action of such reagents as iodine, carbolic acid, &c., whereas sponge—the common and hitherto preferred material for inhalers—is subject to all these changes; and is, hence, wholly unreliable as to the quantity of air-contact surface it will present at a given time, in a given space, and to a given quantity of inhaling substance. Second, by reason of the definite and constant form of the inhaling-tubes, the quantity of air which may be drawn through them is always known or determinate, as well as unvarying, a matter of the highest importance to the physician or other person intending the use of inhalents of a more or less dangerous or powerful nature. Third, the cost of the material of my inhaling instrument as compared with sponge, is as one to sixteen, or thereabout, thus enabling it to be furnished to the trade or medical profession at a much lower price.

Having thus described my invention, what I claim as new, and desire to secure by Letters Patent, is—

1. A core for inhaling-instruments formed of paper.

2. A core for inhaling-instruments, formed of a tube or tubes of bibulous paper or analogous material, as specified.

WILLIAM H. CUTLER.

Witnesses:
JAMES CURGENVEN,
JOHN L. GUITEAU.